US005375158A

United States Patent [19]

Logan

[11] Patent Number: 5,375,158

[45] Date of Patent: Dec. 20, 1994

[54] X-RAY SOURCE FOR MAMMOGRAPHY

[75] Inventor: Clinton M. Logan, Pleasanton, Calif.

[73] Assignee: Regents of The University of California, Oakland, Calif.

[21] Appl. No.: 215,980

[22] Filed: Mar. 21, 1994

Related U.S. Application Data

[63] Continuation of Ser. No. 51,227, Apr. 23, 1993, abandoned.

[51] Int. Cl.[5] ........................ H01J 35/08; G21K 3/00; A61B 6/04

[52] U.S. Cl. ........................................ 378/143; 378/37; 378/156

[58] Field of Search .................. 378/143, 37, 125, 144, 378/156

[56] References Cited

U.S. PATENT DOCUMENTS 3,515,874 6/1970 Bens et al. .............................. 378/37
4,477,921 10/1984 Armini et al. .................. 378/143 X

FOREIGN PATENT DOCUMENTS 2130648 11/1972 France .................................. 378/37

OTHER PUBLICATIONS

UCRL-5200-92-10.11.12, Energy and Technology Review, Oct.-Nov.-Dec. 1992, "Digital Mammograph", C. M. Logan, pp. 27-36.

*Primary Examiner*—David P. Porta
*Attorney, Agent, or Firm*—Henry P. Sartorio; L. E. Carnahan

[57] ABSTRACT

An x-ray source utilizing anode material which shifts the output spectrum to higher energy and thereby obtains higher penetrating ability for screening mammography application, than the currently utilized anode material. The currently used anode material (molybdenum) produces an energy x-ray spectrum of 17.5/19.6 keV, which using the anode material of this invention (e.g. silver, rhodium, and tungsten) the x-ray spectrum would be in the 20-35 keV region. Thus, the anode material of this invention provides for imaging of breasts with higher than average x-ray opacity without increase of the radiation dose, and thus reduces the risk of induced breast cancer due to the radiation dose administered for mammograms.

6 Claims, 3 Drawing Sheets

X-RAY SOURCE FOR MAMMOGRAPHY

The United States Government has rights in this invention pursuant to Contract No. W-7405-ENG-48 between the United States Department of Energy and the University of California for the operation of Lawrence Livermore National Laboratory.

This is a Continuation-In-Part of application Ser. No. 08/051,227 filed Apr. 23, 1994 now abandoned.

BACKGROUND OF THE INVENTION

The present invention is directed to mammographic techniques, particularly to an x-ray source used in screening mammography techniques, and more particularly to an improved x-ray source which produces a higher energy x-ray spectrum which enables mammographic screening breasts with higher than average x-ray opacity without increasing the radiation dose.

Breast cancer, which will eventually strike one out of every nine women in the United State, is a major and growing national health problem. Despite decades of research, the mortality rate for this disease remains high, and its causes are unknown. About 175,000 American women will contract the disease this year, and 45,000 will die of breast cancer (about one person every 12 minutes). For women aged 35 to 50, cancer is the leading cause of death, and breast cancer is the most common malignancy. In addition, the incidence of new breast cancer cases diagnosed in the United States is increasing by about 1.8% each year even when corrected for the general aging of the female population.

Treatment for advanced breast cancer can involve surgery that is disfiguring, relatively high doses of radiation, and potentially toxic drugs with unpleasant side effects. Women undergoing treatment often suffer baldness and early menopause. Even the safety of silicone implants that have been used in breast reconstruction is now in doubt.

On the positive side, survival rates are slowly creeping upwards. Twenty years ago, 68% of women with breast cancer were alive five years after surgery. Today, the five-year survival rate is 77%. Early detection through screening is the most important factor in this improvement, and many studies during the last twenty years have shown that early detection can lead to a high probability of a cure.

By the time breast cancer reaches a size that can be felt as a lump, it has been growing for an average of ten years. The most effective way to detect breast cancer at an early stage is by a physical examination combined with breast x-ray imaging, or mammography. Indeed, mammography is the only means of detecting the microcalcifications that often accompany small, non palpable breast cancers (those that cannot be felt).

Microcalcifications are small grains of calcium-rich mineral deposits in breast tissue. In an estimated 30 to 50% of cases, microcalcifications seen on a mammogram are the first clue to early breast cancer. Up to 80% of breast cancers have associated microcalcifications that can be verified under a microscope. Microcalcifications associated with malignancy are generally less thaw 500 μm in size. Because the mineral deposits absorb x-rays slightly more strongly than do surrounding soft tissues, they are visible in a transmission x-ray image on conventional film at an earlier stage than are soft-tissue masses.

As it is presently practiced, mammography does not detect all breast cancers. Many mineral deposits are faint and subtle on conventional x-ray film., and rather than having distinct edges, they fade gradually into the surroundings. Thus, they can be quite difficult to locate. The potential for oversight is large even when screening is done by the most experienced radiologists.

When directly viewing traditional x-ray film on a light box, a mammographer must systematically search the entire image—by literally using a magnifying glass—to detect all potentially important microcalcifications. Obviously, this type of screening work requires a highly trained (and highly paid) individual. Medical center radiologists estimate that as many as 80% of all women have some calcifications in their breasts. Even though most breasts exhibit some degree of calcification, the presence of deposits alone does not necessarily mean cancer. The size, shape, and distribution of clustered deposits determine whether they represent an indicator for breast cancer in an individual.

In addition, the breast contains many other complex structures that exhibit radiographic contrast, and scratches or spots on the x-ray film can mimic the appearance of microcalcifications. All these factors contribute to the problem of differentiating trouble spots from false alarms. For example, normal breast connective tissue forms linear features in an x-ray image. When two or more such features cross in the image, they may appear as a white spot on film.

Compounding the difficulty of visually spotting significant microcalcifications is the speed at which expert mammographers reach a decision regarding malignancy. At one prominent mammography clinic, 30,000 cases are screened each year, and some radiologists scan up to 300 film records in a single day. The American Cancer Society recommends that a woman between the ages of 40 and 49 have a mammogram every two years and that she do so annually thereafter. If every female in the United States followed this recommendation, 170 million new images would need to be screened each year.

Microcalcifications are often present for reasons other than cancer. However, if the pattern of calcification in an individual is suspicious, then biopsy may be warranted. A biopsy usually means surgical removal of the tissue and subsequent examination under a microscope. Of those women undergoing biopsy as a result of a suspicious mammogram, about one in five have breast cancer.

Using transitional x-ray film screening techniques, which do not apply quantitative criteria, varying interpretations are inevitable, and the miss rate today is fairly high. Indeed, one recent analysis of 320 cases of breast cancer in a screened population revealed 77 cancers (24%) that were missed by screening mammography. In this recent analysis, "missed" is taken to mean that retrospectively, an earlier mammogram revealed a structure or cluster of microcalcifications that are of medical significance. It is common for a breast cancer to be discovered by manual examination even though a mammogram within the preceding year or two has been judged to be negative. In the above-referenced analysis, 19 of the 77 missed cancers (25%) were found by means other than mammography. As it is presently practiced, interpreting mammograms is an exceedingly difficult art.

Most mammograms are obtained with a machine marketed specifically for mammography. Because of the small size and subtle contrast of breast microcalcifications, mammography requires the highest spatial and contrast resolution of any medical x-ray imaging procedure; that is, it requires the best possible image quality. Mammography is also essentially the only medical x-ray imaging procedure routinely done today on a screening basis; thus, it is imperative to use the lowest possible radiation dose.

By looking at the design of the machine itself, including the x-ray source, the required x-ray dose, and the time and money spent on manually interpreting mammograms, there are many areas in need of improvement. Also, given the choice between direct viewing of a film image by a human interpreter (in this case, a mammographer) and quantitative data presentation via computer, there is no natural or logical advantage to direct viewing. In fact, the opposite case can be made. The relation between optical density and the actual object itself is exceedingly complex. Many important physical factors, such as a polychromatic x-ray source, attenuation of photons, statistical noise in the image, and nonlinear optical density in the film, to name only a few, come into play in mammography.

In addition to these physics issues, human physiology and perception must be considered when a human directly interprets a film image. The eye's response to light passing through a film image depends on the observer, making many interpretations and diagnoses subjective. It has been known for decades that the eye and brain are rather good at spotting patterns, especially edges. However, the neural visual system is not very adept at discerning smooth gradients in optical density (discriminating between various shades of gray) or a comparing regions separated in space. This is to say nothing of fatigue, distractions, and other factors that come into play when a mammographer must scan and interpret scores or hundreds of images during a busy day. Even for objects located in adjacent regions, digitizers can measure density differences ten time smaller than those discernible to the unaided eye. In the final analysis, by providing an improved x-ray source, digitizing the data, using a computer to help identify salient features, and then presenting results in creative ways, many features of a film image can be more clearly conveyed.

The x-ray source in conventional mammography typically uses a molybdenum target and filter. Molybdenum (Mo) was selected for largely historical reasons during the development of x-ray tubes, because it is a robust anode material, and because it yields high contrast when used with film. An x-ray generator with an anode made of Mo (often containing some alloying material for longer operating life) produces a relatively low-energy x-ray spectrum that is rich in the Mo characteristic lines at about 17.5 keV and 19.6 keV. This spectrum works well for breasts that are relatively transparent to x-rays, but requires administering sharply increasing radiation doses in order to image breasts with higher than average x-ray opacity, thereby increasing the risk of induced breast cancer via radiation doses for mammograms.

Recently, studies have been made to determine the optimal x-ray energy for mammography, and it was determined that the optimal energy depends not only on the size and composition of the defect to be imaged (such as a large, dense mass versus a small microcalcification), but also on the size and composition of the breast under examination. These studies involved three sizes of breasts: 1) Thin breasts (compressed to 2 cm during imaging), 2) average breasts (5 cm), and 3) thick breasts (8 cm), with all breasts being of average composition (50% adipose and 50% gland). In general, it was found that to image a 100 μm calcification in thin breasts (compressed to 2 cm) the energy was low and the 17.5 keV was sufficient, but if an energy of about 17.5 keV was used to image a 100 μm flaw in a thick breast (compressed to 8 cm), then the radiation dose required was 100 times the dose required in a 2 cm (thin) breast. For average breasts and especially thick, glandular breasts, the desired x-ray energy approached 25 keV. These studies demonstrate that this energy region (25 keV) is also appropriate for imaging a larger 2 mm mass. Such results suggest that the x-ray sources considered best practice today (ones using molybdenum, which emits strongly at 17.5 keV) are poorly suited for mammography. In fact, for the full range of breast-imaging tasks, a source rich in 22 to 25 keV photons is needed.

The present invention satisfies this need by providing an x-ray source or generator, wherein the x-ray spectrum could be adjusted to be rich in the 20 to 35 keV region by the choice of anode material, filtering, and voltage applied to the generator. It has been recognized that by using anode material, such as silver, rhodium, and tungsten, for example, screening mammography can be carried out using low radiation doses regardless of the size and/or composition of the breast being examined, thereby reducing the risk of induced breast cancer.

SUMMARY OF THE INVENTION

It is an object of the present invention to provide an improved x-ray source for mammography.

A further object of the invention is to reduce the risks of induced breast cancer for the radiation dosage administered for mammograms.

Another object of the invention is to provide an x-ray source for mammograms where the x-ray spectrum can be adjusted to be rich in the 20 to 35 keV region.

Another object of the invention is to provide an x-ray generator using an anode material, such as silver, radium, and tungsten, which shifts the output spectrum to higher energy and thereby obtains higher penetrating ability, and thus low radiation doses for breast imaging.

Other objects and advantages of the invention will become apparent from the following description and accompanying drawings. Basically the invention involves an improved x-ray source or generator for mammography. More specifically the invention utilizes a different anode material in the x-ray generator in order to shift the output spectrum to higher energy and thereby obtain higher penetrating ability.

By the use of higher energy and higher penetrating capability, screening mammography can be administered with lower radiation dosage. By using a higher energy output spectrum and lower radiation dosage, mammography can be effectively utilized on breasts of all sizes and composition without increasing the risk of induced breast cancer by the radiation administered. In the x-ray generator of this invention the x-ray spectrum can be adjusted to be rich in the 20 to 35 keV region by the choice of filtering and voltage applied to the generator.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
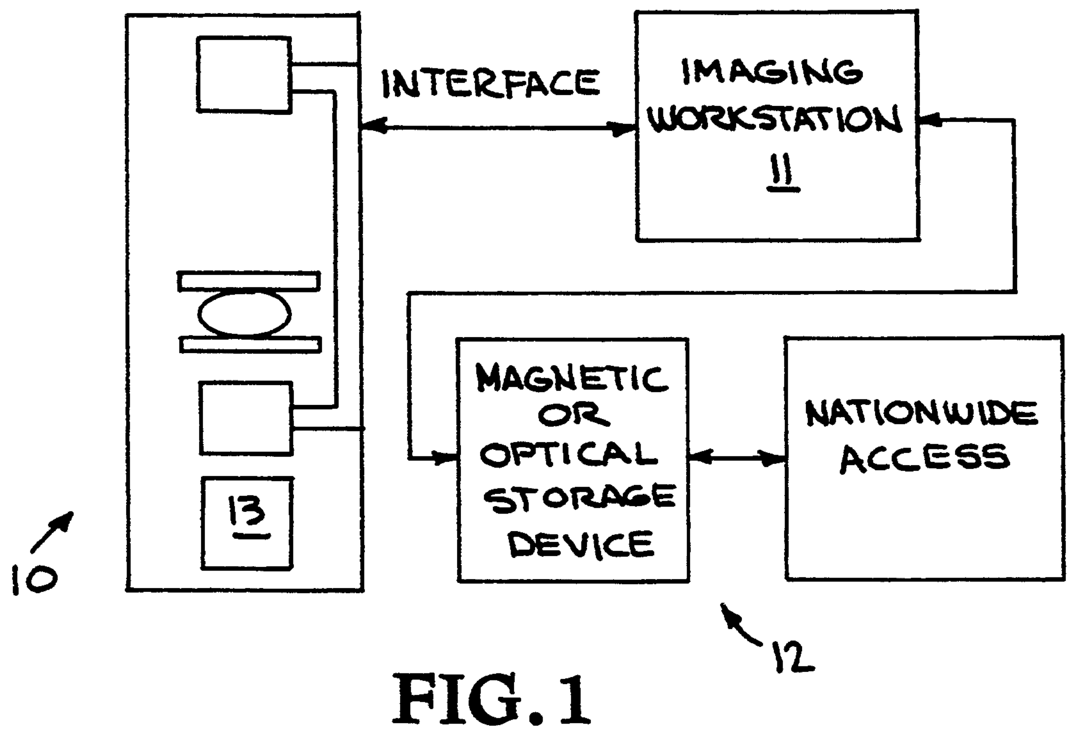
FIG. 1 illustrates an imaging system for screening mammography with components of the x-ray mammography unit of the imaging system can be schematically illustrated.

Screening mammography is a radiological procedure requiring the highest possible image quality at the lowest possible dose. The invention involves an imaging system for screening mammography which utilizes an improved x-ray source or generator wherein the x-ray spectrum can be adjusted to be rich in the 20–35 keV region by the choice of anode filtering, and voltage applied to the generator. Screening mammography exposes breast tissue to ionizing radiation, and therefore to a finite risk of induced cancer. By shifting the output spectrum to higher energy a higher penetrating ability is obtained, there reducing the radiation dose administered for mammograms and thus reduce the risk of induced breast cancer.

The mammography industry is dominated by systems using molybdenum-anode, molybdenum-filtered (Mo/Mo) x-ray spectra and screen-film for image capture. The main reasons for this dominance are that they deliver high-contrast images, dose is acceptable, and Mo is a robust anode material. One undesirable attribute of these systems is that they allow very little spectral tailoring. The spectra are dominated by the Mo-characteristic lines at 17.5 and 19.6 keV. In usual practice, the only spectral adjustment that is made is slight adjustment in the electron accelerating potential (kVp). This adjustment can have strong effect on x-ray contrast, but the Mo-characteristic lines remain the dominant spectral feature. Also, because of the strong absorption from the Mo filter at energies just above 20 keV, it is not possible to heavily populate this spectral region with a Mo/Mo spectrum.

The compromise in system design required in conventional screen-film mammography is enormous. Since the human observer has poor gray-level discrimination, high overall contrast is paramount. Thus much of what is accepted best practice for today's mammography has been driven by the demand for high contrast at the point of display. The choice of the Mo/Mo x-ray spectrum and the characteristics of film, in particular, are driven by the need of high contrast in the image display and the unfortunate fact that the lightbox cannot amplify contrast even if the image has very low noise.

In mammography, it is important for the detector to have both high efficiency and low noise. In digital mammography, a system now under development and uses the improved source of this invention, these conditions would be approached by a charge-coupled device (CCD) camera (see FIG. 1) that is coupled to a scintillator. The function of the scintillator is to convert the x-ray energy to visible light that can then be imaged by the CCD camera. When the condition of low detector noise is met, then random fluctuations in x-rays from the source (changes in fluence) become the limiting factor in determining noise in the image. These random fluctuations are called quantum noise.

If the x-ray energy is too high, sensitivity to variations in the breast vanishes, and the signal of interest becomes very small. If the x-ray energy is too low, few x-rays are transmitted, most are absorbed by the breast, and the image becomes noisy. In addition, because most of the energy is absorbed by the patient as radiation dose, simply increasing x-ray fluence is an unacceptable approach to reducing image noise.

The breast-imaging process has been modeled and the radiation dose that is required to limit quantum noise to a level that will allow reliable detection of the signal has been calculated. This approach uses the Monte Carlo transport code TART to calculate x-ray transmission, scatter, and dose. TART, which is a flexible neutron- and photon-transport code, has been under continuous development at the Lawrence Livermore National Laboratory, University of California, for 30 years. This model allows determination of the optimal x-ray energy for a broad range of breast-imaging tasks.

With a digital mammography system, such as illustrated in FIG. 1, and now under development, contrast is a parameter to be chosen and varied at the point of image display/visualization, not an integral attribute of the entire system. In effect, one is free to perform image processing with a computer rather than by compromising system design. Implicit in this approach is that the appropriate measure of system performance is the dose required to reliably detect a specified flaw and that one will choose to terminate the exposure when sufficient photons have been counted to achieve reliable detection. With a perfect photon-counting detector, reliable detection is not a monatomic function of contrast. Quantum noise can limit detection even though contrast is very high and even very low contrast objects will be imaged if noise is sufficiently low. The situation is profoundly different with a conventional screen-film system since the exposure must continue until a target film density is achieved. For mm-sized flaws with a low x-ray contrast (such as masses) this assures that quantum noise is low (photon counts in a large area are high) and that contrast limits detection. Restating very simply; contrast is the most important measure of spectral performance for screen-film mammography. With a digital system contrast is not useful as a measure of spectral performance. Contrast can be numerically amplified as desired if noise is sufficiently low. Detection of a flaw is achieved when it stands out sufficiently from the noise.

The above-referenced digital mammography system, illustrated in FIG. 1 and which incorporates an x-ray generator made in accordance with the present invention, is described in greater detail in UCRL-52000-92-10.11.12, Energy and Technology Review, October, November, December 1992, pp. 27–36, published February 1993, by the University of California, Lawrence Livermore National Laboratory.

Figure 2:
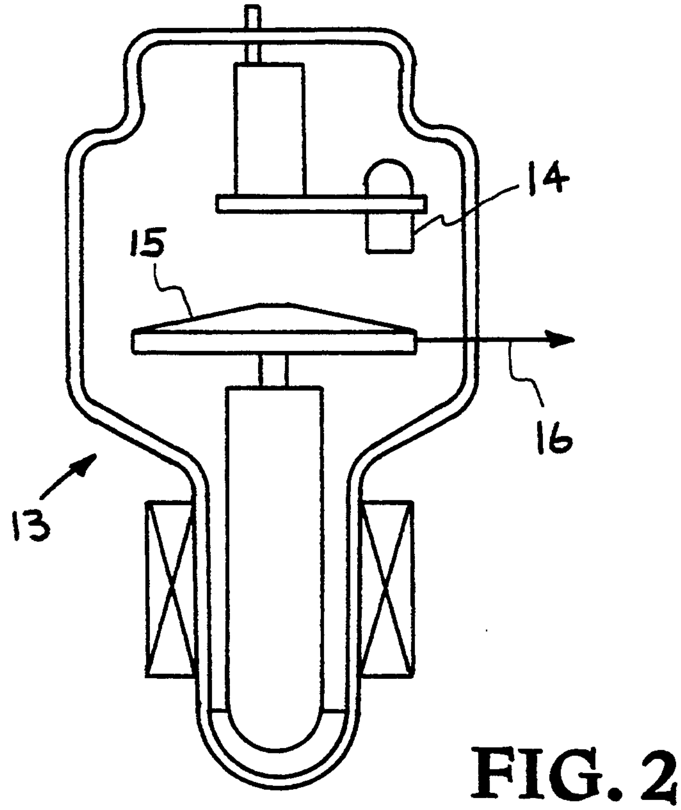
FIG. 2 illustrates an embodiment of a conventional x-ray tube using a rotating anode.

Referring now to the drawings, FIG. 1 illustrates an imaging system for screening mammography which basically comprises an x-ray mammography unit 10, and imaging work station 11, and an image library 12. The x-ray mammography unit 10 includes an x-ray generator or source 13, which may be a rotating anode x-ray tube 13' as illustrated in FIG. 2 and manufactured by the Machlett Laboratories, Inc., or a mammography tube, such as the M151 or the CGR Senograph 500T x-ray tubes, manufactured by Varian, or other x-ray source. X-ray generators, tubes, or other sources, each include, as illustrated in FIG. 2, a cathode 14 and an anode 15, whereby electrons from the cathode 14 strike the anode 15 producing x-rays 16. The construction details and operation of the generator 13 including the cathode and anode do not constitute part of this invention, except for the material of the anode, and thus need not be described, as such details and operation are known in the art. The anode, such as anode 15, of the improved x-ray generator or source 13, is constructed of a higher atomic number material than molybdenum (Mo), and thus the energy of the characteristic lines is shifted to a higher energy. The x-ray spectrum that is rich in the Mo characteristic lines are at an energy of about 17.5 keV and 19.6 keV, while the x-ray spectrum of the higher atomic number material of the present invention can be adjusted to be rich in the 20–35 keV energy region, the energy region being determined by the anode material, the filter, and the voltage applied to the generator.

The invention utilizes two approaches, a first using an anode material of an atomic number somewhat higher than that of Mo (42), and a second using an anode material considerably higher than that of Mo. In the first approach, the anode would be made, for example, of rhodium (Rh) having an atomic number of 45 or silver (Ag) having an atomic number of 47, although other materials of nearby elements, such as palladium (Pd) or cadmium (Cd), or alloys or mixtures of such materials would also be suitable. In the second approach, the anode would be made, for example, of tungsten (W) having an atomic number of 74, although other materials of nearby elements, such as ruthenium (Ru), hafnium (Hf), tantalum (Ta), or rhenium (Re) as well as alloys or mixtures of these materials, would also be suitable. Tungsten is a common anode material for other medical imaging applications, and x-rays sources using tungsten anodes are known.

As pointed out above, the type of anode, the type of filter, and the voltage applied to the generator are factors which determine the energy region of the x-ray spectrum. FIGS. 3–6 illustrate x-ray spectrums of different anode materials and filters. Each of FIGS. 3–6 are graphs showing the relative number of photons as the photon energy (keV) produced by the different anodes/filters.

Figure 3:
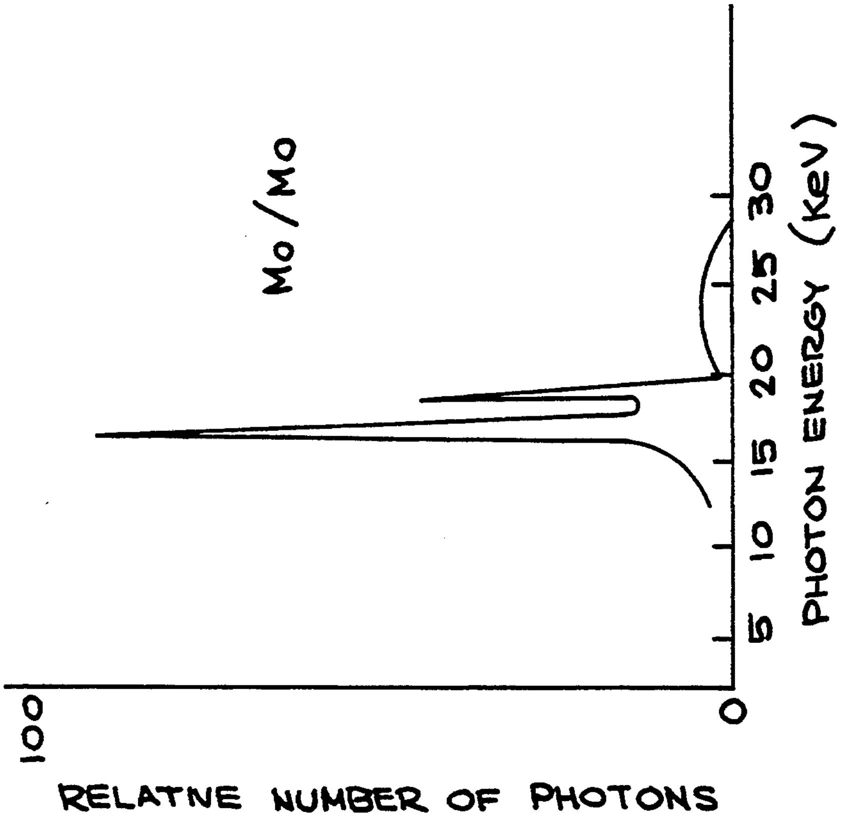
FIG. 3 illustrates an x-ray spectrum produced by a molybdenum anode/molybdenum filter.

FIG. 3 is an x-ray spectrum typical of standard mammography, produced with an Mo anode and filtered with an Mo filter with a thickness of 30 μm, and with electrons accelerated to an energy of 28 keV. The energy x-ray spectrum which is rich in the Mo characteristic lines peaks at about 17.5 keV and 19.6 keV. This energy spectrum works well for breasts that are relatively transparent to x-rays, but requires administering sharply increasing radiation dosage in order to image breasts with higher than average x-ray opacity.

Figure 4:
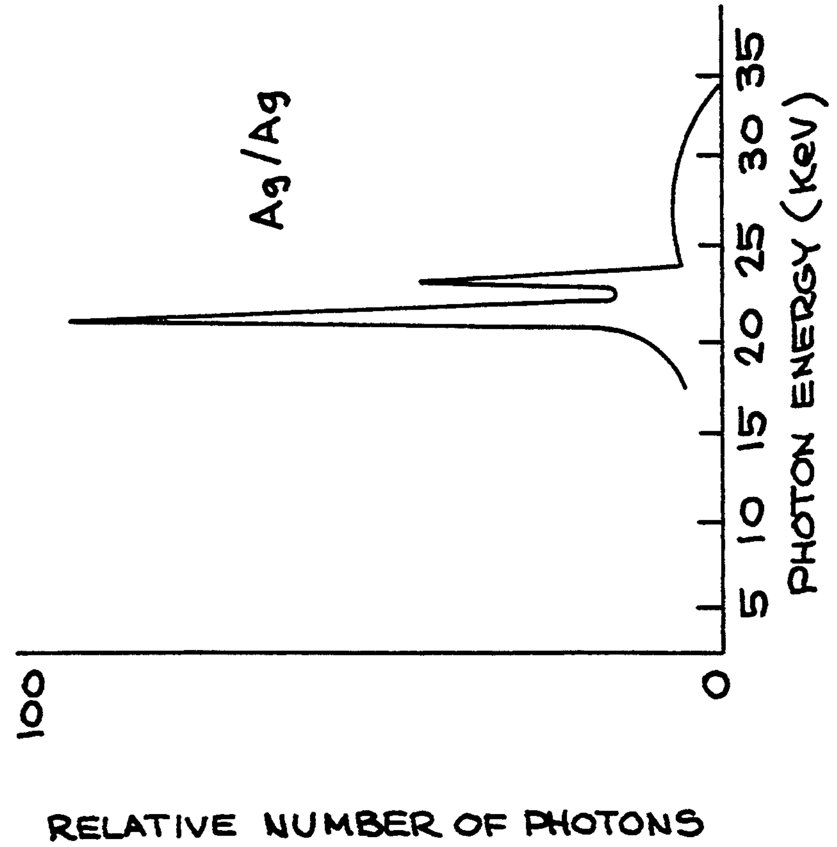
FIG. 4 illustrates an x-ray spectrum produced by an silver anode/silver filter.

FIG. 4 is an x-ray spectrum produced with 34 keV electrons incident on a Ag anode with an Ag filter having a thickness of 30 μm. Here the energy x-ray spectrum contains strong characteristic lines at about 22.1 keV and 25.0 keV.

Figure 5:
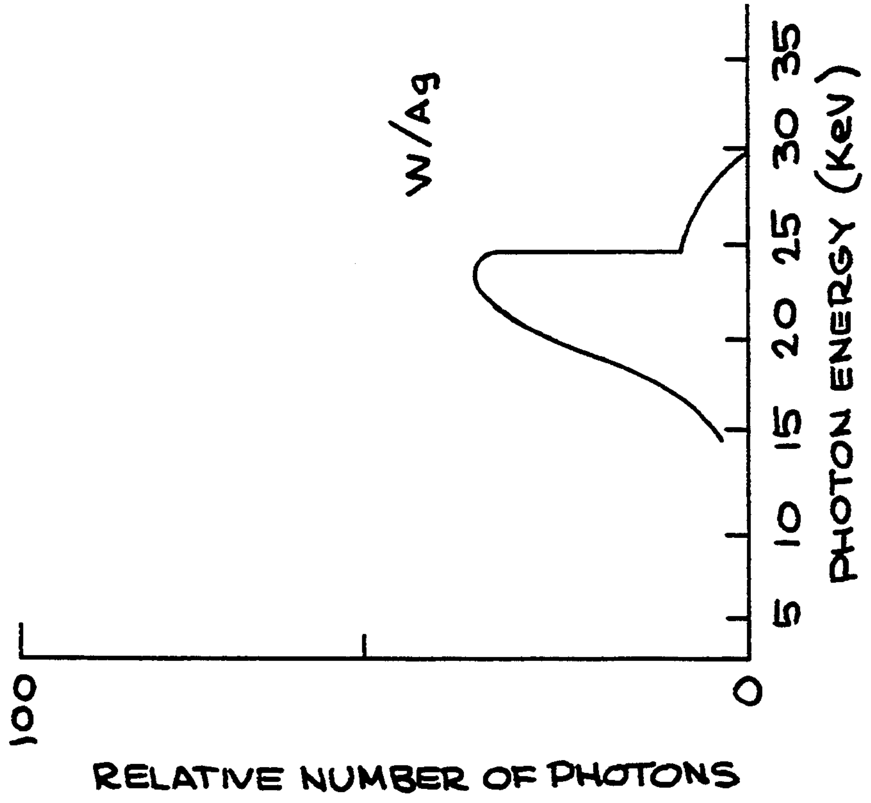
FIG. 5 illustrates an x-ray spectrum produced by a tungsten anode/silver filter.

FIG. 5 is an x-ray spectrum produced with 29 keV electrons incident on a W anode with an Ag filter having a thickness of 30 μm. Here the strong absorption edge of the silver filter causes the energy x-ray spectrum to peak at about 25 keV and tapers to 29 keV.

Figure 6:
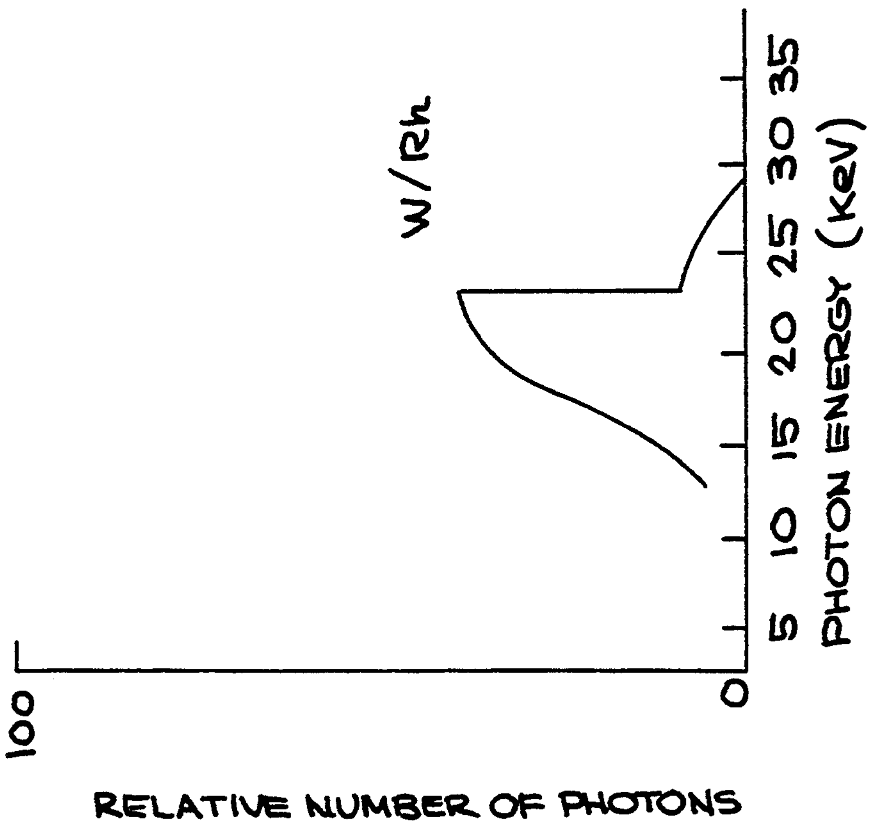
FIG. 6 illustrates an x-ray spectrum produced by a tungsten anode/rhodium filter.

FIG. 6 is an x-ray spectrum produced with 28 keV electrons incident on a W anode with an Rh filter having a thickness of 30 μm. Here the energy x-ray spectrum peaks at about 23 keV and tapers to 28 keV.

Other filter materials such as indium (In), palladium (Pd), and cadmium (Cd) may be used. In images that are limited by photon counting statistics, the most important measure of image quality is the ratio of signal to noise (S/N). The dose required to achieve a specific value of S/N for various photon energies has been calculated. See above-referenced UCRL-5200-92-10.11.12. These calculations show that this invention which is a source rich in 20–25 keV photons, will reduce the dose required to image high opacity breasts (breasts consisting of 50% adipose and 50% glandular tissue and with a compressed thickness of 8 cm), by a factor of seven (7). According to currently accepted models, this will reduce the incidence of induced breast cancer in these types of breasts by the same factor (7). Overall, this invention provides an x-ray source that will reduce induction of breast cancer from mammographic procedures by a factor of 2 to 3.

It has thus been shown, that the present invention provides an x-ray source of screening mammography which substantially advances the state of the art by enabling such screening with low radiation dosage regardless of the size and/or composition of the breast being imaged, thereby reducing the risk of induced breast cancer. Also, it has been established that this invention will provide an x-ray source for the full range of breast-imaging tasks, which need a source rich in 22–25 keV photons.

While specific examples of anode materials have been set forth to explain the principle of the invention, such are not intended to be limiting. Modifications and changes will become apparent and it is intended that the scope of the invention be limited only by the scope of the appended claims.

What is claimed is:

1. An improved imaging system for reducing radiation dosage during screening mammography of human breasts compressed to greater than 5 cm, including an x-ray source having a cathode and an anode, the improvement comprising:
   - an anode composed of silver, and
   - a filter means including a filter constructed of silver and having a thickness of about 30 μm,
   - said anode producing an x-ray spectrum containing strong characteristic lines at about 22.1 keV and 25.0 keV, and wherein electron energy incident thereon is 34 keV,
   - said x-ray spectrum having energy sufficient for imaging human breasts compressed to 2–8 cm during imaging without increased radiation dosage during imaging of human breasts compressed to greater than 5 cm.

2. An improved x-ray source for mammography for imaging human breasts compressed to 2–8 cm during imaging without increased radiation dosage, and which produces an x-ray spectrum adjusted to be rich in the 22.1–25.0 keV photon region, said improved x-ray source including at least:
   - a cathode,
   - an anode fabricated from silver,
   - filtering means including a filter material constructed of silver and having a thickness of about 30 μm, and means for applying voltage such as to produce electrons incident on said anode at an energy of about 34 keV, said anode producing said x-ray spectrum rich in the 22.1–25.0 keV photon region, whereby imaging of human breasts compressed to greater than 5 cm during imaging is accomplished without substantial increased radiation dosage over that used in imaging of human breasts compressed to 2 cm.

3. A method for screening mammography of human breasts without increase of radiation dosage irrespective of the breast size, comprising:

compressing the breasts to be imaged to 2–8 cm, producing an x-ray spectrum rich in the 22.1–25.0 photon region, and irradiating the thus compressed breasts with the thus produced x-ray spectrum to enable imaging of human breasts irrespective of size without increase in radiation dosage when imaging breasts compressed to greater than 5 cm.

4. The method of claim 3, wherein producing the x-ray spectrum carried out by providing an x-ray source which includes a cathode, an anode, a filtering means, and means for applying voltage such as to produce electrons incident on the anode at an energy of about 34 keV.

5. The method of claim 4, additionally including forming the anode from silver, and providing the filtering means with a filter constructed of silver and having a thickness of about 30 μm.

6. The method of claim 3, wherein producing the x-ray spectrum rich in the 22.1–25.0 photon region is carried out by providing an x-ray source including an anode composed of silver, a filter composed of silver and having a thickness of about 30 μm, and means for applying voltage such as to produce electrons incident on said silver anode at an energy of about 34 keV, whereby imaging of human breasts compressed to greater than 5 cm can be carried out without increasing the radiation dosage applied to the breasts.

* * * * *